United States Patent [19]

Baum et al.

[11] Patent Number: 5,252,064
[45] Date of Patent: Oct. 12, 1993

[54] SUBGINGIVAL IRRIGATOR

[75] Inventors: John W. Baum; Len Haferman; James M. Jennings; Anna J. Russell; Gary Thomas, all of Fort Collins, Colo.

[73] Assignee: Teledyne Industries, Inc., Fort Collins, Colo.

[21] Appl. No.: 657,649

[22] Filed: Feb. 19, 1991

[51] Int. Cl.5 .................. A61C 17/02; A61C 1/10; A61C 3/02; A61C 1/12
[52] U.S. Cl. ........................................ 433/80; 433/85; 433/88
[58] Field of Search .............. 433/80, 84, 85, 88, 433/89, 90; 604/118, 140, 141, 143, 237, 415; 222/382, 631

[56] References Cited

U.S. PATENT DOCUMENTS

| 2,794,437 | 6/1954 | Tash | 604/415 |
|---|---|---|---|
| 3,089,490 | 3/1960 | Goldberg | 604/237 |
| 3,768,472 | 8/1973 | Hodosh et al. | 128/218 P |
| 3,827,147 | 8/1974 | Condon | 433/90 |
| 3,854,209 | 12/1974 | Franklin et al. | 604/143 |
| 4,007,739 | 2/1977 | Bron et al. | 128/218 R |
| 4,276,880 | 7/1981 | Malmin | 433/80 |
| 4,303,070 | 12/1981 | Ichikawa et al. | 128/218 P |
| 4,319,568 | 4/1982 | Tregoning | 604/123 |
| 4,512,769 | 4/1985 | Kozam et al. | 604/209 |
| 4,592,728 | 6/1986 | Davis | 433/80 |
| 4,636,198 | 1/1987 | Stade | 604/154 |
| 4,645,488 | 2/1987 | Matukas | 604/59 |
| 4,650,475 | 3/1987 | Smith et al. | 604/189 |
| 4,673,396 | 6/1987 | Urbaniak | 604/211 |
| 4,770,632 | 9/1988 | Ryder et al. | 433/28 |
| 4,821,923 | 4/1989 | Skorka | 222/80 |
| 4,861,340 | 8/1989 | Smith et al. | 604/141 |
| 4,869,720 | 9/1989 | Chernack | 604/228 |
| 4,969,874 | 11/1990 | Michel et al. | 604/140 |

OTHER PUBLICATIONS

The Right Tool, Electron Fusion Devices, Inc. (date unknown).

Primary Examiner—Gene Mancene
Assistant Examiner—Cindy A. Cherichett
Attorney, Agent, or Firm—Hugh H. Drake

[57] ABSTRACT

A barrel serves as a reservoir in which a treatment fluid is to be contained and within which barrel is a slideable plunger. A connector at one end of the barrel is receptive to attachment of a cannula. Another connector is located at the other end of the barrel. A housing has a coupling attachable to that other connector. On the housing is a detachable fitting receptive of a hose which delivers air under pressure. Included in the housing is an adjustable air pressure regulator in an air flow path between the detachable fitting and the coupling with the regulator being selectively adjustable to control the flow of the air in that path. Associated with the irrigator is a container for the treatment fluid and which includes a pump sealingly attachable to the one end of the barrel for delivering the fluid into the reservoir in response to movement of the barrel.

14 Claims, 7 Drawing Sheets

SUBGINGIVAL IRRIGATOR

The present invention relates to subgingival irrigators. More particularly, it pertains to a subgingival irrigation handpiece which delivers a steady, controllable amount of treatment fluid as well as to an associated canister-pump for facilitating the loading of the reservoir.

The dental profession has long recognized the need to be concerned with more than just the exposed surfaces of the teeth. Necessary also is the examination and treatment of the base of the teeth as well as the surrounding gum tissue. From the rudimentary approach of using a swab to apply treatment fluid to the periodontal area, the art has progressed to include probing of the periodontal pocket and thoroughly flushing that pocket with pulsating irrigation apparatus in order to clean and also to apply medications.

Dental professionals have used syringes for delivering medicants directly to specific sites along the teeth. This requires facile operation in use of the syringe along with manipulation of the gum tissues, and it is difficult to apply the treatment fluid evenly and surely. It also has at least usually required a two-handed operation to reload the syringe as a result of which for that purpose the person administering the treatment must withdraw from the patient.

It is a general object of the present invention to provide a new and improved subgingival irrigator and associated apparatus.

Another object of the present invention is to provide a subgingival irrigator which affords the treatment administrator additional flexibility of control by taking advantage of use of a footswitch already available in connection with the usual dentalequipment air supply.

A further object of the present invention is to provide a new and improved subgingival irrigator in which loading of a reservoir may be accomplished with use of but a single hand of the treatment administrator.

A correlated object of all of the foregoing is to provide a new and improved subgingival irrigator which accomplishes the foregoing aims and objectives and yet which is durable, reliable and cost effective.

A subgingival irrigator handpiece in accordance with the present invention includes a barrel which serves as a reservoir in which a treatment fluid is to be contained. Slideable within the barrel is a plunger movable from one end to the other. One connector at one end of the barrel is receptive to attachment of a cannula. There is another connector at the other barrel end and a housing attachable to that other connector. Also in the housing is a detachable fitting receptive of a hose which delivers air under pressure. The delivery is controllable by a foot-operated switch.

In the housing is an adjustable air-pressure regulator located in the air flow path between the fitting and the other coupling for selectively controlling the flow of the air in that path. Desirably associated with the irrigator handpiece itself is a treatment-fluid container having a delivery pump sealingly securable to the one connector and exhibiting single-stroke operation actuable by movement of the coupled barrel.

The features of the present invention which are believed to be patentable are set forth with particularity in the appended claims. The organization and manner of operation of two specific embodiments of the invention, together with further objects and advantages thereof, may best be understood by reference to the following description taken in connection with the accompanying drawings in the several figures of which like numerals identify like elements, and in which :

Figures 1, 2:
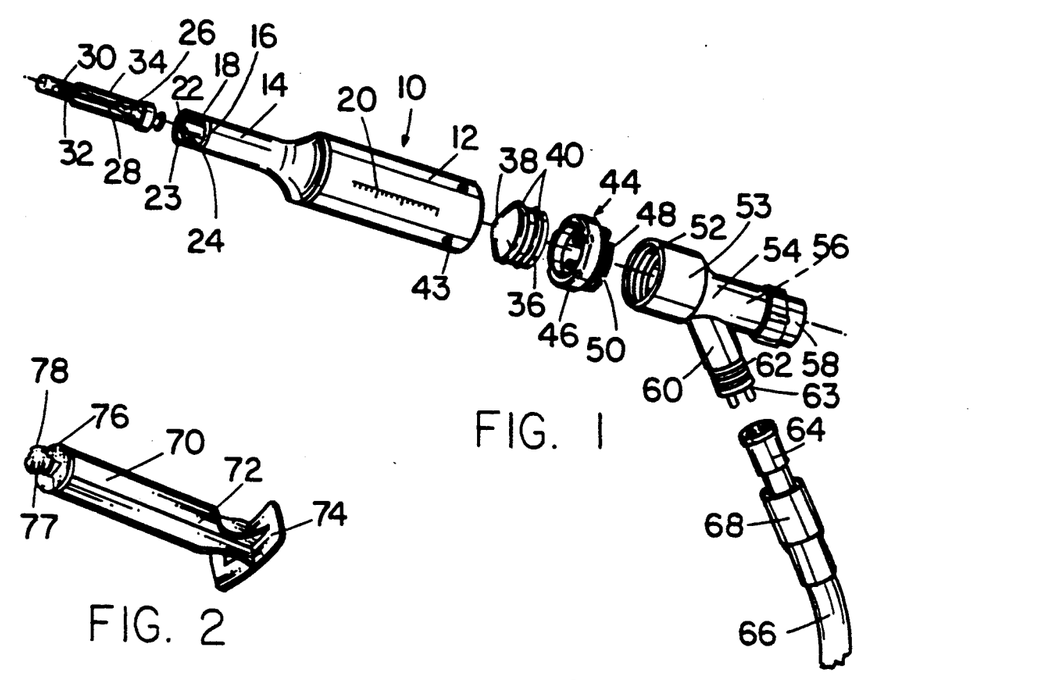
FIG. 1 is an exploded isometric view of a subgingival irrigator associated with an air-supply hose.
FIG. 2 is an isometric view of a retractor employed with the irrigator of FIG. 1.

With reference first to FIG. 1, a subgingival irrigation handpiece 10 has a reservoir 12 in the shape of a hollow barrel on one end of which is pressed a sleeve 14 that curvingly tapers to a narrower end 16 on which is affixed a female luer-lock fitting 18. A scale 20 is located along the wall of reservoir 12 and preferably calibrated in cubic centimeters or millileters as indicated. Preferably, reservoir 12 is made of Phillips HGN200 polypropylene.

Fitting 18 preferably is conventional as adopted for the securement of known cannulas and other needlelike treatment and dispensing devices. It is provided with a central, cylindrical hollow tube 22 surrounded by an outer tube 23 the inner side wall of which at 24 has a double lead thread. Attachable onto tube 22 is a cannula 26 which is in the form of a hollow needle 28 having a closed, smoothly-rounded end 30 adjacent to which in the side wall of needle 28 is an opening or port at 32. Alternatively, the needle may have a port in its end. For maintaining sterile conditions, cannula 26 is encased in a protective cover 34 except when in use.

Slideable within the barrel of reservoir 12 is a cylindrical plunger 36 which has a nose 38. On the external surface of plunger 36 are a pair of integrally-formed, spaced sealing rings 40. Plunger 36 and sleeve 14 are formed entirely of a resilient synthetic rubber, preferably Santoprene by Monsanto which is a thermoplastic elastomer composed of a combination of polypropylene and ethylene propylene.

Circumferentially-spaced around the outer wall of reservoir 12 near the rear end thereof are, in this case, a plurality of four posts 43. Slideable onto the outer surface of reservoir 12 from its forward end is a retaining ring 44 which has at its forward end a collar 46 from which rearwardly project a circumferentially-spaced series of externally threaded fingers 48 between each successive one of which is a channel 50 that on being mounted slides around a respective one of posts 43. On assembly, fingers 48 engage within threads 52 inside a hollow swivel 53 mounted on one end of a housing 54 which contains a regulator 56 controlled by a rotatable knob 58.

Depending downwardly at an angle towards the rear, as an integral part of housing 54, is an air connector stub 60. In this case, an adaptor 62 is secured at the lower end of stub 60 for connection through a gasket 63 to a standard 4-hole fitting 64 on the remote end of the standard air hose 66 leading from the conventional dental operatory. That operatory typically supplies air for driving the usual dental tools including drills, grinders, polishers and other workpieces which form part of the standard dental equipment for use in treating the patient. A footswitch controls the flow of the air between on and off. A sleeve 68 on hose 66 is pulled up and secured to the threads shown on the external surface of adaptor 62. Similar usable adaptors are provided for other dental fittings one type of which includes a fifth hole to accommodate a fiber-optic element. A quick-connect fitting will be described in connection with FIG. 7. In preparing for use of the irrigator, air supply hose 66 is connected by mating fitting 64 to adaptor 62 and with the inclusion of a gasket 63 to form an air seal. Sleeve 68 is twisted onto adaptor 62.

FIG. 2 illustrates a retractor 70 in the form of an elongated shank 72 across one end of which is a finger-piece 74. The user may place his first two fingers on respective opposite sides on the back of finger-piece 74 with the thumb on the front in order most easily to move retractor 70 longitudinally. Projecting from the other end of shank 72 is a strut 76 across the outer end of which is a circular plate 77. A circumferential-spaced plurality of lugs 78 project radially from the perimeter of plate 77.

The interior of plunger 36 is hollow and its inner sidewall is provided with a corresponding plurality of inwardly-directed circumferentially-spaced tabs each of which defines a ledge on its inner side and which has a stop at one end. The user may insert lugs 78 into the slots between the tabs and slightly rotate retractor 70 to seat the respective lugs on the corresponding ledge and against the stop to create a bayonet-type interlock and thereby be able to move the plunger into and out of reservoir 12.

Figure 3:
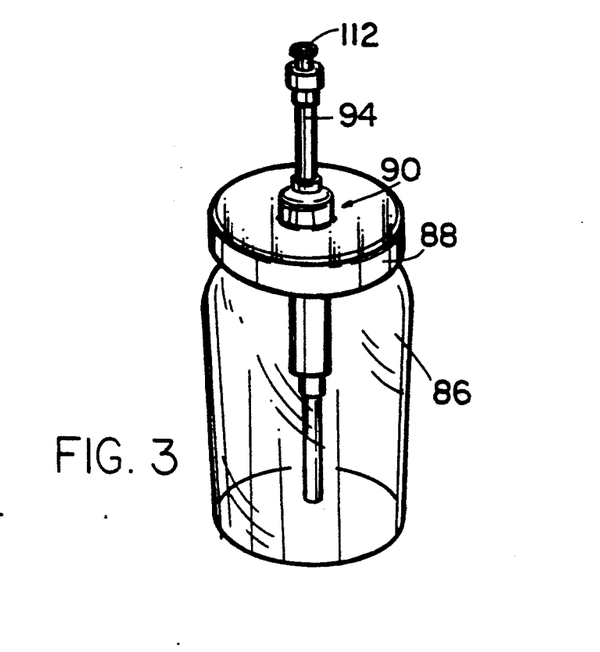
FIG. 3 is an isometric view of a supply container and its associated delivery pump.
Figure 4:
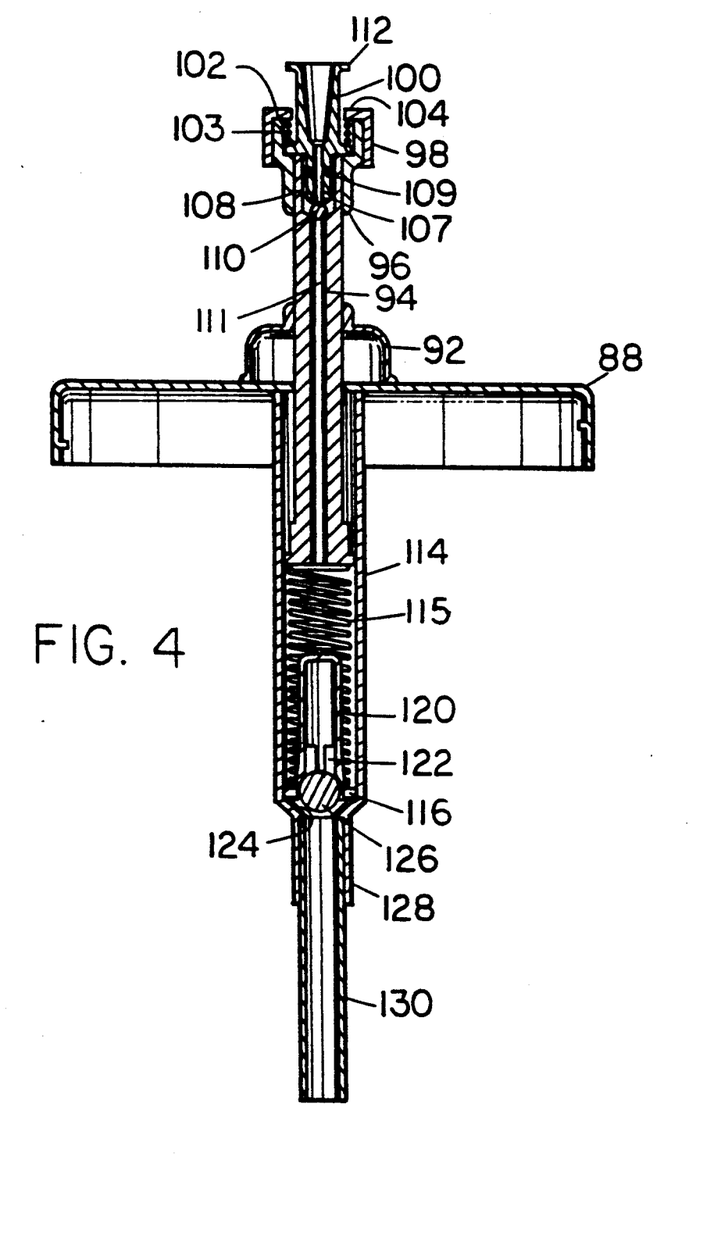
FIG. 4 is a longitudinal cross-sectional view of a portion of the pump unit included in FIG. 3.

Depicted in FIGS. 3 and 4 is a bottle 86 for holding a supply of fluid such as sterile water or medicant to be used for patient treatment. Bottle 86 is closed at its upper end by a screw-on cap 88 through which extends a pump assembly 90. Secured centrally atop cap 88 is a mounting guide 92 through which is guided a hollow pump stem 94 on the upper end of which is mounted an adaptor 96. Mounted in turn on the upper end of adaptor 96 is seated a collar 98. Disposed internally within adaptor 96 is a male luer-lock fitting or connector 100 which captivates a compression spring 102 between a seat 103 formed internally around the lower end of fitting 100 and an internal rim 104 on collar 98. A narrower lower hollow shank 107 of fitting 100 is moveable within an enlarged bore 108 of the upper end portion of stem 94 and is sealed therewithin by an 0-ring 109. At the bottom of bore 108 is seated a ball 110 atop the upper end of the internal passage 111 through stem 94. A peripheral flange 112 on the upper end of fitting 100 serves as the male thread interlockable with fitting 18 leading to reservoir 12.

Depending downwardly from the undersurface of cap 88 is a sleeve 114 within which an enlarged lower end of stem 94 is movable and beneath which is captivated a compression spring 115 seated at its bottom on the lower end rim 116 of an insert which has an upwardly projected hollow-dome 120 in the lower end of which are a circumferentially-spaced series of flutes 122. Mounted within flutes 122 at and above a seat 124 formed at the lower end of sleeve 114 is a ball 126. Ball 126 moves downwardly against seat 124 which is formed by a necked-down portion of sleeve 114 that continues a short distance further at 128 and on which mounts an extension 130 at its lower end.

With the parts positioned as shown in FIG. 4, pushing on fitting 100 to move stem 94 downwardly will cause fluid within container 86 to be forced upwardly through passage 111 around ball 126. However, the escape of the fluid is blocked by ball 110 which is held in a closed position by spring 102. When fitting 18 at the end of reservoir sleeve 14 is affixed, however, connector 112 is pulled upwardly relative to adaptor 96. That frees ball 110 to allow fluid to escape upwardly and on into reservoir 12 for filling. When pump pressure is thereafter relaxed, ball 126 closes against seat 124 and prevents the back flow of the fluid just pumped upwardly. Flutes 122 are shaped at their lower ends to limit upward movement of the ball but yet permit the passage of fluid upwardly during pumping.

The reservoir, reservoir sleeve and plunger to be used as well as the cannula will have been autoclaved, chemiclaved or otherwise sterilized. It is significant to note that the specific materials identified above are fully compatible with steam or chemical sterilization and disinfection. Those materials or their equivalents must be used to avoid rapid deterioration. More than one plunger and reservoir may be prepared at the same time for extended treatment during a single procedure. The sterilizing steps may tend to unduly dry plunger 36 as a result of which, from time to time, it should be lubricated with a material such as silicone.

Plunger 36 is inserted into the large open end of reservoir 12. Retractor 70 is pushed into the interior of plunger 36 and turned clockwise after which plunger 36 should be driven completely forward into the reservoir and then withdrawn by twisting the plunger clockwise as the retractor is pulled back.

In order to fill the reservoir from canister 86, plunger 36 is again inserted into the large opening of reservoir 12. Either the retractor or the upper end of the stem and valve assembly at connector 100 may then be used to push plunger 36 into a forward and ready position for filling.

Cap 88 with its pump assembly is removed from canister 86 and the latter is filled with an irrigating solution. For later reference, the canister should be labeled with the type of solution contained. Cap 88 is threaded back onto canister 86. The pump assembly is primed by grasping the outside of the valve assembly and connecting fitting 18 on the end of reservoir sleeve 14., threading the latter clockwise when screwed downwardly until there is securement. Holding the reservoir and canister firmly, stem 94 is pushed down several times until the solution begins to flow into the reservoir. The pump will need to be primed each time canister 86 is refilled.

To fill a reservoir, the luer-lock fitting 18 of the reservoir being filled is secured to fitting 100 on the pump by engagement and clockwise rotation. Holding reservoir 12 firmly, it is pushed down several times until the reservoir is filled to the desired level as measured in milliliters or cubic centimeters in accordance with scale 20. Reservoir 12 should not be filled beyond the markings on the scale, because an overfilling of the reservoir may cause the irrigating solution to spurt out from the reservoir when it is subsequently engaged to regulator housing 54. After reservoir 12 is filled, and fitting 18 has been disconnected, any air should be expelled from the reservoir by pushing plunger 36 slightly forward.

A second filling method is to engage retractor 70 with plunger 36 after which plunger 36 is pushed into the forward and ready position for filling. The forward end of sleeve 14 with fitting 24 is inserted into a cup or beaker in which the treatment solution has been placed. Retractor 70 is then withdrawn in order to fill reservoir 12, any air being expelled at the end of that proceeding by pushing the plunger forward. Retractor 70 may then be disconnected.

When desired, the irrigating solution may be warmed prior to use even while it is in the reservoir by allowing the filled reservoir to stand in warm water. Very short-duration microwave heating also may be used in accordance with the manufacturers + recommendation for microwave heating of the irrigant.

The filled reservoir may then be engaged with regulator housing 54 after retaining ring 44 has been removed. Grasping the retaining ring, it is moved over the forward end of 12 and on toward housing 54 so that the four posts 43 on reservoir 12 slide within the corresponding four slots 50 on retaining ring 44 with a reservoir seal 140 in place (FIG. 5) and preferably lubricated with silicone. Ring 44 is attached to swivel 53 by threading the retaining ring clockwise as viewed from the forward end of the handpiece, being secured tightly to guard against leaking. Any air leak at this point of joinder is a warning that the retaining ring and the regulator are not properly assembled or may be coming loose.

Holding cannula 28 by its protective sheath 34, the cannula is attached to fitting 18 on reservoir sleeve 14 by threading clockwise until the cannula is secured in place. Sheath 34 is saved for use upon disassembly.

To adjust fluid flow, control knob 58 may be turned clockwise as viewed from the rear in order to increase flow or counter-clockwise to obtain less flow. Markings preferably are provided to indicate high, medium and low flow rates. Depending upon the viscosity of the irrigating solution, it may be necessary to vary the size or gauge of the cannula in order to get the desired rate of flow.

In use, the patient is seated with his or her head tilted at a comfortable angle to minimize flow of the solution downwardly into the throat and evacuation is utilized. With the apparatus assembled and using the cover, cannula 28 may be gently bent to whatever angle is desired to provide accurate and easy placement of the solution.

The flow rate is adjusted as desired in accordance with its viscosity. For example, water or PERIDEX solution have a very low viscosity and therefore usually require lower settings. Using the fingers against the edge of the mouth to establish a fulcrum, the irrigator is held by the professional as he or she would hold the usual drill or other hand-held instrument. Cannula 28 is inserted below the gingival margin at the selected site. The irrigant solution is then released by stepping on the footswitch, that release being stopped when the fluid begins to flow back out of the periodontal pocket. Usually, it will be preferred to irrigate both the facial and lingual services. Preferably, periodontal charting will be employed in order to determine sites for irrigation and the amount of irrigant and type used will be recorded for future reference.

After the treatment procedure, reservoir 12 should be disconnected from swivel 53. Retractor 70 is employed with plunger 36 to purge reservoir 12 of any unused solution after which both the reservoir and plunger are rinsed, leaving the parts ready for sterilization. It is recommended that the plunger not be installed within the reservoir during sterilization or storage. After disconnection from air hose 66, the entire regulator assembly is also then ready for sterilization at which time adjustment knob 58 should be set at its low flow rate position. Of course, canister 86 and pump assembly 90 also should be thoroughly rinsed, cleaned and disinfected before reuse.

Figure 5:
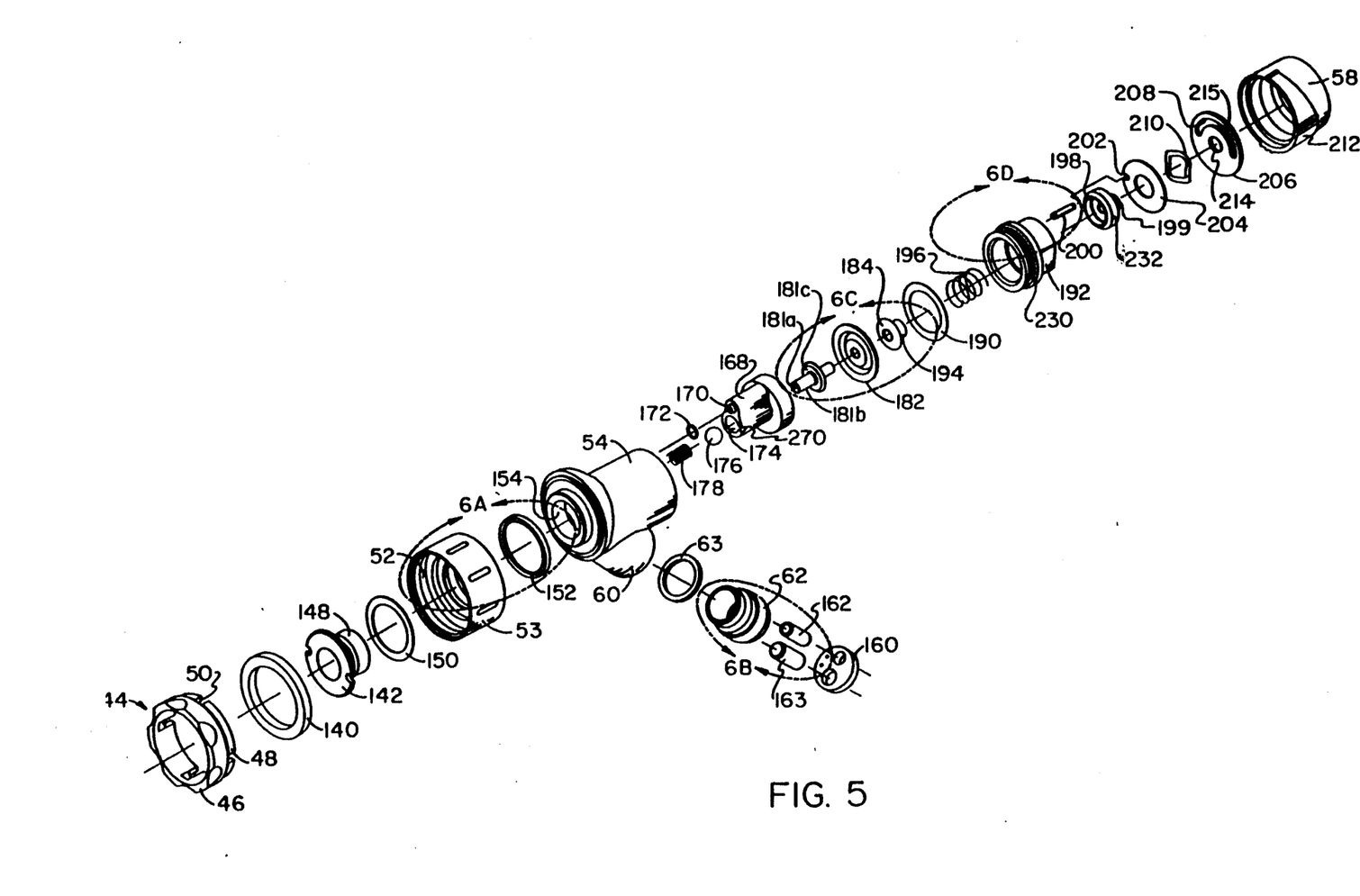
FIG. 5 is an exploded isometric view of a regulator assembly which is a part of the irrigator of FIG. 1.
Figure 6A:
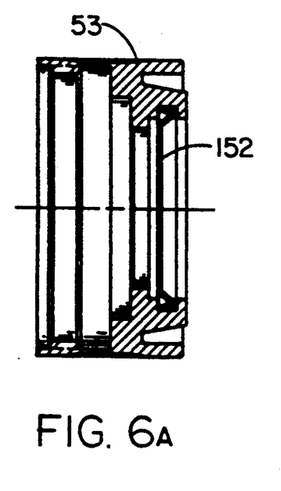
FIG. 6A is a cross-sectional view of an assembly of a group of the components designated by the circle 6A in FIG. 5.

FIG. 5 illustrates the parts as exploded apart so as to reveal their spatial relationship as they are assembled. For the most part, visible threads indicate that which is threaded into another component. As compared with FIG. 1, reservoir 12, sleeve 14 and luer-lock fitting 18 are not included. Beginning at the left is retaining ring 44 which threads into the bore of swivel 53 and seals against a washer 140. A swivel mount 142 has a cylinder 148 which projects through a washer 150, through an opening in the bottom of swivel 53 and beyond that through sealing ring 152 into an opening 154 in the body of housing 54. The orientation of sealing ring 152 within swivel 53 is detailed in FIG. 6A.

Figure 6B:
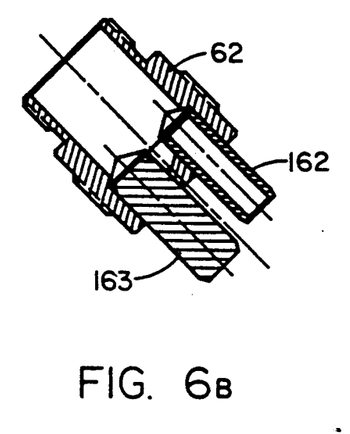
FIG. 6B is a cross-sectional view of an assembled group of components indicated by the circle 6B in FIG. 5.

Adaptor 62 fits through gasket 63 into the bottom of stub 60. Seated through a washer 160 and staked into receiving holes in the bottom of adaptor 62 is a tube 162 and a solid pin 163 with that securement being illustrated in FIG. 6B.

Figure 7A:
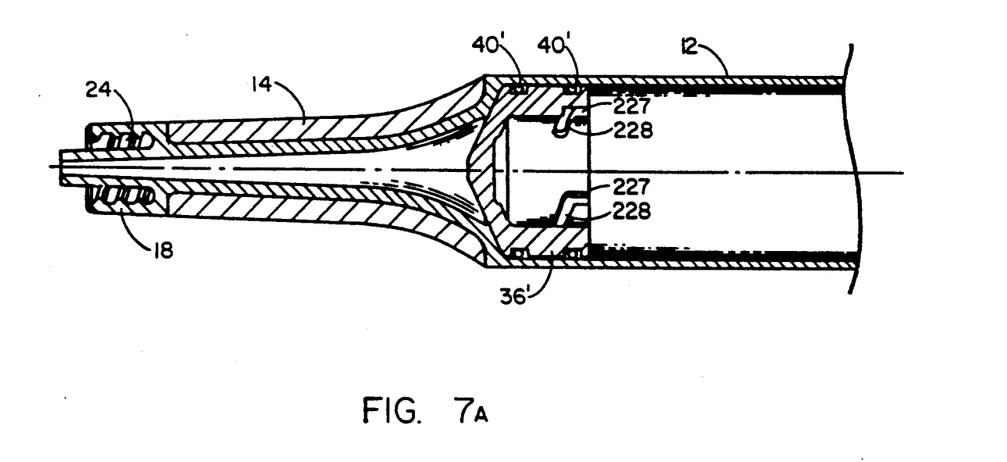
FIGS. 7A and 7B together present a crosssectional view of an assembled subgingival irrigator of another embodiment of the subgingival irrigator representing the overall manner of the assembly also of the embodiment shown in FIG. 1.
Figure 7B:
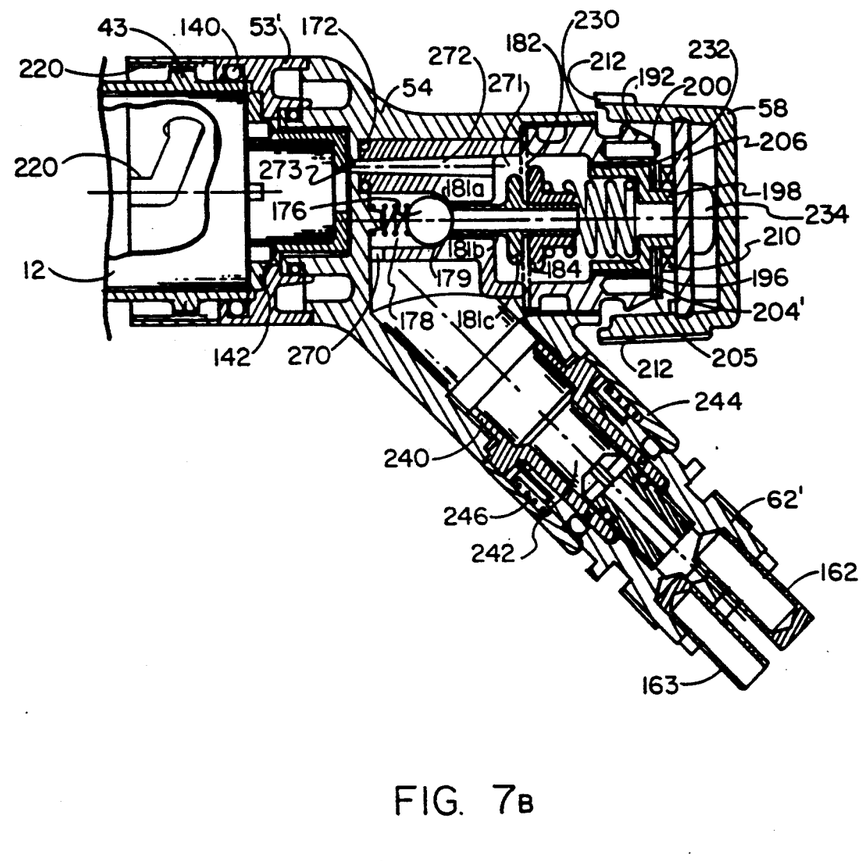

To the rear beyond regulator housing 54 is an insert 168 from which a snout 170 projects forwardly through an O-ring 172 into a well defined in a forward internal housing wall better seen in FIG. 7B. Seated into a well 174 located in the forward end of insert 168 is a bal 1 176 urged rearwardly by a compress ion spring 178 the other end of which is seated on a boss projecting rearwardly from that internal housing wall in housing 54. Well 174 is necked down at its bottom to define a seat 179 for ball 176 which in this case is made of stainless steel.

Figure 6C:
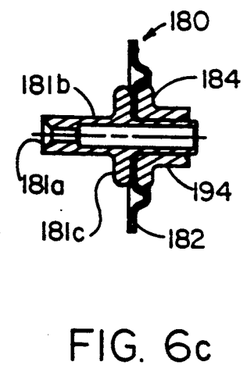
FIG. 6C is a cross-sectional assembly view of another group of assembled components indicated by the circle 6C in FIG. 5.

Fitting into the rear end of insert 168 is an assembly 180 having a seat-shaped seal 181a on the end of a tube 181b intermediate the length of which is formed a ring 181c. Ring 181c is clamped against one side of a diaphram 182 on the other side of which is clamped a grommet 184. The outer rim of diaphram 182 presses against a washer 190 which seats against the forward face of a nut 192 that threads into the rear end of housing 54. FIG. 6C illustrates the details of orientation and clamping of diaphram 182 relative to tube 181b and grommet 184.

Figure 6D:
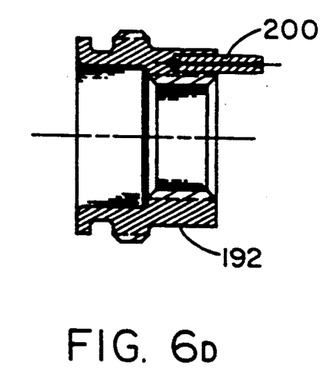
FIG. 6D is a cross-sectional view of a group of the assembled components indicated by the circle 6D in FIG. 5.

Seated on a hollow boss 194 at the rear of grommet 184 is a spring 196 the other end of which lodges into the bottom of a forwardly-facing well in an externally-threaded adjuster 198. Projecting from the rear of adjustor 198 is a boss 199. As detailed in FIG. 6D, a pin 200 staked into one circumferentialportion of the rear face of nut 192 projects through a notch 202 in the perimeter of a washer 204. Further to the rear is a retainer 206 having a circumferentialsector slot 208 within which rides the rear end of pin 200. Sandwiched between washer 204 and retainer 206 is a resilient wave washer 210. Bringing up the rear end is knob 58 which includes over a portion of its rear external surface a raised wedge-shaped island 212 the thickness of which in the longitudinal direction corresponds to the difference between high and low pressure.

The external surface of boss 199 is knurled. On assembly, a central opening 214 in retainer 206 is press fit onto the knurled surface of boss 199 which fixes the retainer in place. Knob 58 is made of a hard rubber, preferably the same Santoprene material as used for sleeve 14, and the periphery 215 of retainer 206 is finely teethed. When the knob is pressed onto the retainer a tight affixation is obtained. Thus, rotation of knob 58 causes rotation of adjuster 198 in its thread and consequent fore and aft movement of the base or seat of spring 196 and, therefore, the setting of diaphram 182.

A further understanding of the manner of assembly will be gained by reference to FIGS. 7A and 7B wherein the parts are fully assembled and in which parts corresponding to those in FIG. 5 have been fully assembled. Reservoir 12, sleeve 14, luer-lock fitting 18 and a modified plunger 36' have been added. With respect to the latter modified plunger as well as to retaining ring 44 as previously described, a portion of the regulator and the air hose adaptor, however modifications have been illustrated in FIGS. 7A and 7B as a result of which FIGS. 7A and 7B represents an embodiment alternative at of FIGS. 1-5. Nevertheless, FIGS. 7A and 7B serve also to illustrate the overall nature of the first-described embodiment as assembled.

Figure 8:
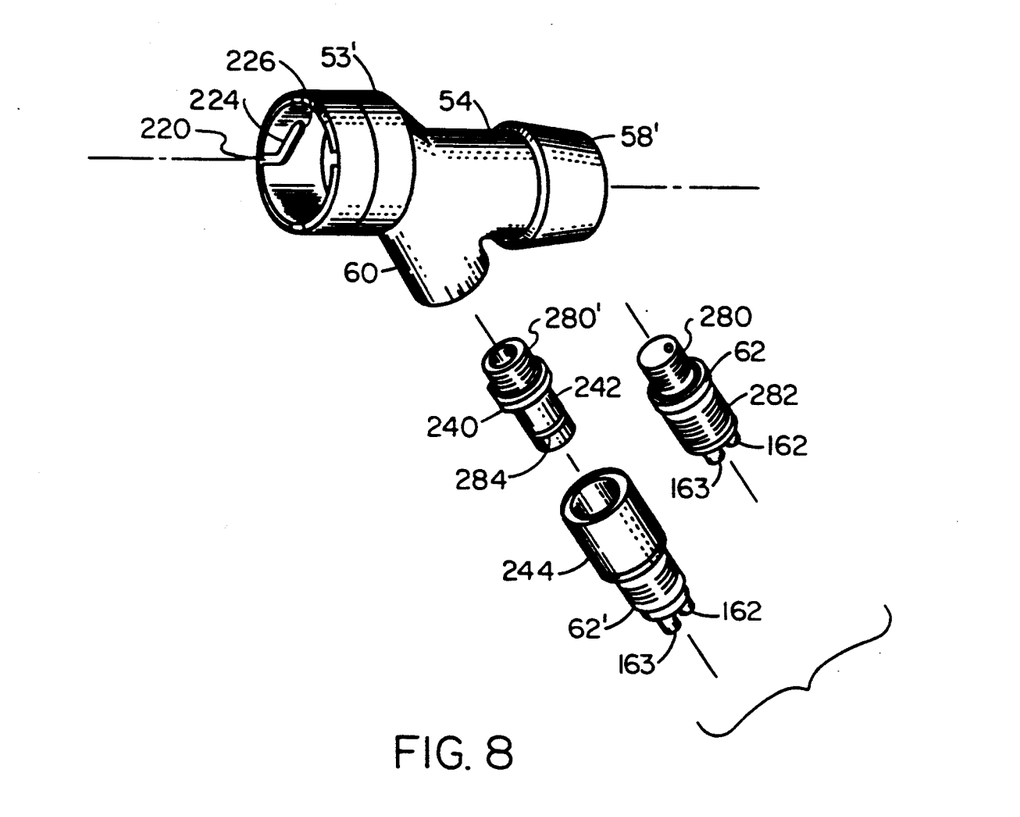
FIG. 8 is an isometric exploded view showing a modified component for the assembly of FIG. 7 associated with a variety of different attachment fittings.

In this modification for mounting reservoir 12 to swivel 53', the forward facing inner wall of swivel 53' has four axially-directed slots 220 aligned correspondingly with posts 43 on reservoir 12. As seen in FIG. 8, each of slots 220 at its inner end turns about 70° laterally into a continuation 224 which ends at a terminating 226 that on relative twisting seats a post 43. Thus, retaining ring 44 of the other embodiment is eliminated and a direct bayonet-type coupling is used. The mounting arrangement of FIG. 7 is less preferred because of the increased likelihood during use of dismounting reservoir 12 from swivel 53.

Another modification resides in plunger 36' which has the same overall shape as before but in this case has separate O-rings 40' and a revised receptor arrangement for lugs 78 on retractor 70. In this case, analogous to slots 220 and their extensions, three slots 227 project axially inward of the rear end of the plunger and then turn laterally as at 228 to accommodate twisting and seating of lugs 78.

As indicated by the corresponding numbers, thermal regulator portion of the handpiece shown in FIG. 7B is largely similar to that of FIG. 5. The primary difference is that washer 204 is replaced by a modified washer 204' which has a circumferentially-spaced series of detent holes that mate with a like series of nubs formed on a cam plate 205 secured by Pin 200 against rotation with respect to housing 54. In the preferred embodiment of FIGS. 1-5, that detent function is eliminated. It may be noted that threaded engagements are denoted at 230 and 232. A torquing lock 234 is provided at the rear of the assembly for holding the forward components tightened together.

The embodiment of FIG. 7B illustrates a different air hose coupling having a conventional quick-connect arrangement. In this case, the adaptor includes an externally threaded snout 240 which is received within the threaded opening at the bottom of stub 60 and continues outwardly into a nipple 242. Mounted around an adaptor 62' is a sleeve 244 moveable longitudinally relative to adaptor 62' but loaded by a spring 246 so as normally to be in a position that clamps nipple 242 in connection. By pulling sleeve 244 toward stub 60, nipple 242 is allowed to be removed while adaptor 62' is still coupled to air hose 66. Any other form of detachable air hose coupling may be substituted.

It will be observed that ball 176 along with seat 179 form a check valve located in the air flow path. Spring 178 urges the ball valve member in the closed direction. Diaphram 182 is another resilient element flexural either way about a center position. Nut or adjuster 198 serves to bias spring 196, and thus diaphram 182, in a direction that, in turn, biases seal 181a toward closure to prevent air escape through tube 181b. Ball 176 and its seat 179 are open or closed as determined by the respective spring constants and the amount of bias imposed by adjustor 198.

Regulator operation is the same in either embodiment. Diaphram 182 urges ball 176 toward an open position, while spring 178 urges that ball toward a closed position against its seat. Air pressure enters through stub 60 and enters the chamber ahead of the ball through a small slot 270 in insert 168. Adjusting knob 58 toward a higher pressure setting forces grommet 184 and assembly 180 in a direction to increase the tendency toward opening of ball 176. As air from the air supply pressurizes regulator stub 60, air flows through slot 270 in insert 168 past ball 176 and along the outside of assembly 180. A chamber 271 within insert 168 and alongside diaphram 182 then becomes pressurized. That pressure then forces air out snout 170 through a channel 272 in insert 168, through an aligned hole 273 in body housing 54 and into the space between the body housing 54 and plunger 36.

The pressure between body housing 54 and plunger 36 will continue to increase until the corresponding and equal pressure in chamber 271 reaches a level sufficiently high to move diaphram 182 back against spring 196 and close the air path between the ball 176 and chamber 271. If sometime later plunger 36 moves forward in reservoir 12, then the pressure in the space between plunger 36 and body housing 54 will be reduced. This reduction in pressure will also reduce the pressure in chamber 271. This pressure feedback system cause the pressure on plunger 36 to approach a nearly constant level at whatever setting is dialed by use of knob 58.

To summarize, rotation of knob 58 adjusts the spring 196 force. Spring 196 pushes assembly 180 which contacts ball 176 and moves it off seat 179. As ball 176 leaves seat 179 air may now flow from the air source, past ball 176 and seat 179 through chamber 271 and out channel 272. As long as the spring 196 force as selected by the knob 58 position exceeds the force on assembly 180 from air pressure, then air flow will be maintained as described above. If the force on assembly 180 from incoming air pressure exceeds the spring 196 force then assembly 180 is moved in the direction to compress spring 196. As assembly 180 moves to compress spring 196 it also disengages from ball 176. Without assembly 180 holding ball 176 off seat 179, incoming air pressure seats ball 176 onto seat 179 and stops all air flow from the air source. Any remaining air pressure in air chamber 271 is bled off through channel 272. As air pressure is bled off, spring 196 force again forces ball 176 off seat 179 and the process or cycle continues or repeats. It is this method of balancing spring force on one side of the diaphram with air pressure and its resulting force on the other side of the diaphram which enables the air pressure to be regulated.

The maximum pressure permitted is positively limited by the extent of slot 208 to that which is established to be safe for guarding against injury to the patient. That is a distinct improvement over the use of hand-operated syringes whereby a very high pressure may be created by accident or improper use.

With all its features, the handpiece is still light in weight. It also is sufficiently small that it may be stored in the standard mount provided for other typical hand-operated dental tools.

Finally, FIG. 8 illustrates housing 54 of the second embodiment with swivel 53' and including a simplified knob 58' at one end. This view illustrates the alternative embodiment wherein slots 220 with lateral extensions 224 are included for the purpose of receiving directly posts 43 on reservoir 12. For coupling into the bottom of stub 60, at the right is positioned an adaptor 62 threaded externally at 280 and 282 for connection to the stub and hose sleeve 68. To the left of adaptor 62 is a representation of the quick-connect fitting shown in FIG. 7 and discussed in the description with respect thereto. It again has an upward threaded portion 280' screwed into the bottom of stub 60 and a nipple 242 with a locking recess 284. Both versions are threaded mateably with air hose sleeve 68.

Notwithstanding that there are a fairly large number of parts included in the overall handpiece. They are so formed that everything which contacts the medicant is readily detachable and severable to permit sterilization by conventional processes. The cooperation between the diaphram, springs and the ball valve enables a simple and yet effective kind of regulation function to be performed. In use, the total combination is highly desirable to the dental professional who is enabled to accomplish even one-handed loading of a reservoir when desired.

In terms of economy, it will be observed from the exploded views that all parts are capable of being ordinarily manufactured, while the assembly of the parts is an operation of the simplest nature. At the same time, the parts in themselves are of sufficient strength and durability to ensure long-lasting reliability.

Patient safety has been carefully accommodated. Limiting maximum pressure by means of the regulator overcomes the danger posed by hand operation of an ordinary syringe, air pressure is bled off directly or through tube 181b to the rear and out from beneath the wall of knob 58.

While particular embodiments of the invention have been shown and described, and various alternatives and modifications have been taught, it will be obvious to those skilled in the art that changes and modifications may be made without departing from the invention in its broader aspects and in view of the invention as a whole. Therefore, the aim in the appended claims is to cover all such changes and modifications as fall with in the true spirit and scope of that which is patentable.

We claim:

1. A hand-held subgingival irrigator comprising:
a barrel in which a treatment fluid is to be contained;
a plunger slideable within said barrel;
a connector at one end of said barrel and receptive to attachment of a cannula;
a housing having a coupling attachable to the other end of said barrel and defining a space between said plunger and said housing;
a fitting on said housing detachably receptive of a hose which delivers air under pressure;
and an adjustable air pressure regulator in said housing in an air flow path between said fitting and said coupling to selectively control the flow of air in said air path and automatically maintain substantially constant the pressure in said space at a selected level as said plunger moves within said barrel.

2. A hand-held subgingival irrigator as defined in claim 1 which further includes an air flow switch and a source of air under pressure with said switch being located remotely from the operative location of said housing.

3. A hand-held subgingival irrigator as defined in claim 2 wherein said air flow switch is a footswitch.

4. A hand-held subgingival irrigator as defined in claim 1 in which said plunger has a rearwardlyopening hollow interior the walls of which define a first part of an interlock a bayonet-type rotational which further includes a separate retractor having an elongated shank on one end of which is disposed an array of surfaces formed to define a second part of said rotational interlock interengageable with said first part for moving said plunger within said barrel.

5. A hand-held subgingival irrigator as defined in claim 1 in which said plunger is made of a sterilizable thermoplastic elastomer composed of a combination of polypropylene and ethylene propylene and said barrel is made of a sterilizable polypropylene.

6. A hand-held subgingival irrigator comprising:
a barrel in which a treatment fluid is to be contained;
a plunger slideable within said barrel;
a connector at one end of said barrel and receptive to attachment of a cannula;
a housing having a coupling attachable to the other end of said barrel;
a fitting on said housing detachably receptive of a hose which delivers air under pressure;
and an adjustable air pressure regulator in said housing in an air flow path between said fitting and said coupling to selectively control the flow of air in said air path; said regulator further including:
a check valve, having a valve member and a valve seat, located in said air flow path;
a first spring tending to urge said valve member toward closure with said valve seat;
a flexible diaphram one side of which is exposed to the pressure of air in said path between said seat and said coupling;
an element coupled to said one side of said diaphram and movable thereby to push said valve member away from said valve seat;
a second spring coupled to the other side of said diaphram and tending to urge flexure of said diaphram and movement of said element in a direction to open said check valve;
and an adjustor for selectively biasing said second spring in control of the amount of said air in said flow.

7. A hand-held subgingival irrigator as defined in claim 6 in which said adjustor includes a manually controllable knob mounted on the end of said housing opposite said coupling.

8. A hand-held subgingival irrigator comprising:
   a barrel in which a treatment fluid is to be contained;
   a plunger slideable within said barrel;
   a connector at one end of said barrel and receptive to attachment of a cannula;
   a housing having a coupling attachable to the other end of said barrel;
   a fitting on said housing detachably receptive of a hose which delivers air under pressure;
   and an adjustable air pressure regulator in said housing in an air flow path between said fitting and said coupling to selectively control the flow of air in said air path; said regulator further including:
   a check valve, having a valve member and a valve seat, located in said air flow path;
   a first spring tending to urge closure of said valve member and valve seat;
   a flexible diaphram one side of which is exposed to pressure in said air flow path between said seat and said coupling;
   an element coupled to said one side of said diaphram and moveable thereby in one direction to open said check valve, an increase in said pressure tending to effect movement of said element in a direction opposite said one direction;
   an assembly coupled to the other side of said diaphragm and tending to urge flexure of said diaphram and movement of said element in said one direction to open said check valve;
   and an adjustor for selectively biasing the flexure of said diaphram in control of the amount of said air flow.

9. A hand-held subgingival irrigator as defined in claim 8 in which said element is a hollow tube communicating with the exterior of said housing.

10. A hand-held subgingival irrigator comprising:
    a barrel in which a treatment fluid is to be contained;
    a plunger slideable within said barrel;
    a connector at one end of said barrel and receptive to attachment of a cannula;
    a housing having a coupling attachable to the other end of said barrel and defining a space between said plunger and said housing;
    a fitting on said housing detachably receptive of a hose which delivers air under pressure;
    an adjustable air pressure regulator in said housing in an air flow path between said fitting and said coupling to selectively control the flow of air in said path and automatically maintain substantially constant the pressure in said space at a selected level as said plunger moves within said barrel;
    a container for holding a supply of said treatment fluid;
    a pump coupled to said container with an inlet immersed in said fluid and an outlet external to said container;
    a connector element included in said outlet and connectable with said barrel connector for fluid flow;
    and said pump being operable to move said fluid from said container into said barrel when said connector barrel is pushed toward said container.

11. A hand-held subgingival irrigator as defined in claim 10 in which said pump includes inlet and outlet check valves with said inlet check valve preventing backflow of said fluid from said barrel and in which said outlet check valve is closed except when said connector element is connected to said barrel connector.

12. A subgingival irrigator comprising:
    a barrel open at one end and in which a treatment fluid is to be contained;
    a plunger sealingly slideable within said barrel with said plunger having a rearwardly-opening hollow interior the walls of which define a first part of a bayonet-type rotational interlock.
    and a retractor having an elongated shank on one end of which is disposed an array of surfaces formed to define a second part of said rotational interlock interengageable with said first part for moving said plunger within said barrel.

13. For use in filling the reservoir of a subgingival irrigator with said reservoir having one part of a two-part interlock, the supply system comprising:
    a container for holding a supply of a treatment fluid;
    a pump coupled to said container with an inlet immersed in said fluid and an outlet external to said container;
    a second part of said interlock included on said outlet;
    and said pump being operable to move said fluid from said container into said reservoir when the parts of said interlock are engaged and said reservoir is pushed toward said container.

14. A supply system as defined in claim 13 in which said pump includes inlet and outlet check valves switch said inlet check valve preventing backflow of said fluid from said reservoir and in which said outlet check valve is closed except when said first and second parts are interengaged to complete said interlock.

* * * * *

UNITED STATES PATENT AND TRADEMARK OFFICE
CERTIFICATE OF CORRECTION

PATENT NO. : 5,252,064
DATED : October 12, 1993
INVENTOR(S) : Baum, et al

It is certified that error appears in the above-indentified patent and that said Letters Patent is hereby corrected as shown below:

Column 1, line 24: "al so" should read -- also --.

Column 1, line 25: " two-hand ed" should read -- two-handed --.

Column 1, line 36: "dentalequipment" should read -- dental- equipment --.

Column 2, line 60: "entirety" should read -- entirely --.

Column 5, line 27: "manufacturers +" should read -- manufacturer's --.

Column 6, line 6: "services" should read -- surfaces --.

Column 6, line 45: "bal 1 176" should read -- ball 176 --.

Column 6, line 46: "compress ion" should read -- compression --.

Column 6, line 68: "circumferentialportion" should read -- circumferential-portion --.

Column 7, line 3: "circumferentialsector" should read -- circumferential-sector --.

UNITED STATES PATENT AND TRADEMARK OFFICE
CERTIFICATE OF CORRECTION

PATENT NO. : 5,252,064
DATED : October 12, 1993
INVENTOR(S) : Baum, et al

It is certified that error appears in the above-indentified patent and that said Letters Patent is hereby corrected as shown below:

Column 7, line 30: after "however", a comma (,) should be inserted.

Column 7, line 32: "represents" should read -- represent --.

Column 7, line 41: "terminating" should read -- termination --.

Column 7, line 56: "thermal" should be cancelled and replaced by -- the --.

Column 7, line 62: "Pin" should read -- pin --.

Column 10, line 25: "rearwardlyopening" should read -- rearwardly-opening --.

Column 10, line 27: "an interlock a bayonet-type rotational" should read -- a bayonet-type rotational interlock --.

UNITED STATES PATENT AND TRADEMARK OFFICE
CERTIFICATE OF CORRECTION

PATENT NO. : 5,252,064
DATED : October 12, 1993
INVENTOR(S) : Baum, et al

It is certified that error appears in the above-indentified patent and that said Letters Patent is hereby corrected as shown below:

Column 11, lines 2 and 3: "manuallycontrollable" should read -- manually-controllable --.

Column 12, line 46: "switch" should read -- with --.

Signed and Sealed this

Twenty-fourth Day of May, 1994

Attest:

BRUCE LEHMAN

Attesting Officer

Commissioner of Patents and Trademarks